(12) United States Patent
Bayer et al.

(10) Patent No.: US 8,182,422 B2
(45) Date of Patent: May 22, 2012

(54) ENDOSCOPE HAVING DETACHABLE IMAGING DEVICE AND METHOD OF USING

(75) Inventors: Lex Bayer, Palo Alto, CA (US); Rupesh Desai, San Jose, CA (US); John Higgins, Los Altos, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 945 days.

(21) Appl. No.: 11/609,838

(22) Filed: Dec. 12, 2006

(65) Prior Publication Data

US 2007/0142711 A1  Jun. 21, 2007

Related U.S. Application Data

(60) Provisional application No. 60/750,325, filed on Dec. 13, 2005, provisional application No. 60/761,475, filed on Jan. 23, 2006, provisional application No. 60/772,442, filed on Feb. 9, 2006, provisional application No. 60/802,056, filed on May 19, 2006.

(51) Int. Cl.
*A61B 1/05* (2006.01)
*A61B 1/06* (2006.01)

(52) U.S. Cl. ........ 600/175; 600/109; 600/113; 600/129; 600/173; 600/181

(58) Field of Classification Search ............ 600/127, 600/129, 160, 172, 175, 182, 102, 109, 113, 600/173, 107, 170, 112, 247, 248, 181; 433/30, 433/31
See application file for complete search history.

(56) References Cited

U.S. PATENT DOCUMENTS

| | | | |
|---|---|---|---|
| 1,500,798 A * | 7/1924 | Campodonico | 433/31 |
| 1,509,041 A * | 9/1924 | Hyams | 433/29 |
| 3,437,747 A | 4/1969 | Sheldon | |
| 3,610,231 A | 10/1971 | Takahashi et al. | |
| 3,643,653 A | 2/1972 | Takahashi et al. | |

(Continued)

FOREIGN PATENT DOCUMENTS

CN  1 628 603  6/2005

(Continued)

OTHER PUBLICATIONS

International Search Report for PCT/US2008/069435, filed Jul. 8, 2008, mailed Oct. 23, 2008, 8 pgs.

(Continued)

*Primary Examiner* — John P Leubecker
(74) *Attorney, Agent, or Firm* — Morrison & Foerster LLP

(57) ABSTRACT

An endoscope assembly with a main imaging device and a first light source is configured to provide a forward view of a body cavity, and further includes a detachable imaging device with an attachment member engageable with the distal end region of the endoscope, a linking member connected to the attachment member, and an imaging element with a second light source, wherein the detachable imaging device provides a retrograde view of the body cavity and the main imaging device. Light interference is reduced by using polarizing filters or by alternating the on/off state of the main imaging device, the first light source, the imaging element and the second light source so that the main imaging device and first light source are on when the imaging element and second light source are off and the main imaging device and first light source are off when the imaging element and second light source are on.

41 Claims, 11 Drawing Sheets

U.S. PATENT DOCUMENTS

| | | | |
|---|---|---|---|
| 3,739,770 A | 6/1973 | Mori | |
| 3,889,662 A | 6/1975 | Mitsui | |
| 3,897,775 A | 8/1975 | Furihata | |
| 3,918,438 A | 11/1975 | Hayamizu et al. | |
| 4,261,344 A | 4/1981 | Moore et al. | |
| 4,327,711 A * | 5/1982 | Takagi | 600/139 |
| 4,351,587 A * | 9/1982 | Matsuo et al. | 359/647 |
| 4,398,811 A | 8/1983 | Nishioka et al. | |
| 4,494,549 A * | 1/1985 | Namba et al. | 600/109 |
| 4,573,450 A | 3/1986 | Arakawa | |
| 4,586,491 A | 5/1986 | Carpenter | |
| 4,625,236 A | 11/1986 | Fujimori et al. | |
| 4,646,722 A | 3/1987 | Silverstein et al. | |
| 4,699,463 A * | 10/1987 | D'Amelio et al. | 385/118 |
| 4,721,097 A | 1/1988 | D'Amelio | |
| 4,727,859 A * | 3/1988 | Lia | 356/241.5 |
| 4,741,326 A | 5/1988 | Sidall et al. | |
| 4,790,295 A * | 12/1988 | Tashiro | 600/176 |
| 4,800,870 A | 1/1989 | Reid, Jr. | |
| 4,825,850 A | 5/1989 | Opie et al. | |
| 4,836,211 A | 6/1989 | Sekino et al. | |
| 4,846,154 A | 7/1989 | MacAnally et al. | |
| 4,852,551 A | 8/1989 | Opie et al. | |
| 4,853,773 A | 8/1989 | Hibino et al. | |
| 4,862,873 A | 9/1989 | Yajima et al. | |
| 4,867,138 A | 9/1989 | Kubota et al. | |
| 4,869,238 A | 9/1989 | Opie et al. | |
| 4,870,488 A | 9/1989 | Ikuno et al. | |
| 4,873,572 A | 10/1989 | Miyazaki et al. | |
| 4,873,965 A | 10/1989 | Danieli | |
| 4,884,133 A | 11/1989 | Kanno et al. | |
| 4,899,732 A | 2/1990 | Cohen | |
| 4,905,667 A | 3/1990 | Foerster et al. | |
| 4,907,395 A | 3/1990 | Opie et al. | |
| 4,911,148 A | 3/1990 | Sosnowski et al. | |
| 4,911,564 A | 3/1990 | Baker | |
| 4,915,626 A * | 4/1990 | Lemmey | 433/31 |
| 4,926,258 A | 5/1990 | Sasaki | |
| 4,947,827 A | 8/1990 | Opie et al. | |
| 4,947,828 A | 8/1990 | Carpenter et al. | |
| 4,979,496 A | 12/1990 | Komi | |
| 4,991,565 A | 2/1991 | Takahashi et al. | |
| 5,010,876 A * | 4/1991 | Henley et al. | 600/112 |
| 5,019,040 A | 5/1991 | Itaoka et al. | |
| 5,025,778 A * | 6/1991 | Silverstein et al. | 600/104 |
| 5,026,377 A * | 6/1991 | Burton et al. | 606/108 |
| 5,050,585 A | 9/1991 | Takahashi | |
| RE34,110 E | 10/1992 | Opie et al. | |
| 5,159,446 A | 10/1992 | Hibino et al. | |
| 5,166,787 A * | 11/1992 | Irion | 348/75 |
| 5,178,130 A | 1/1993 | Kaiya et al. | |
| 5,187,572 A | 2/1993 | Nakamura et al. | |
| 5,193,525 A | 3/1993 | Silverstein et al. | |
| 5,196,928 A | 3/1993 | Karasawa et al. | |
| 5,253,638 A | 10/1993 | Tamburrino et al. | |
| 5,260,780 A | 11/1993 | Staudt, III | |
| 5,271,381 A | 12/1993 | Ailinger et al. | |
| 5,305,121 A | 4/1994 | Moll | |
| 5,318,031 A | 6/1994 | Mountford et al. | |
| 5,329,887 A | 7/1994 | Ailinger et al. | |
| 5,337,734 A | 8/1994 | Saab | |
| 5,381,784 A | 1/1995 | Adair | |
| 5,406,938 A * | 4/1995 | Mersch et al. | 600/138 |
| 5,434,669 A | 7/1995 | Tabata et al. | |
| 5,443,781 A | 8/1995 | Saab | |
| 5,447,148 A | 9/1995 | Oneda et al. | |
| 5,483,951 A | 1/1996 | Frassica et al. | |
| 5,494,483 A * | 2/1996 | Adair | 600/111 |
| 5,518,501 A | 5/1996 | Oneda et al. | |
| 5,520,607 A | 5/1996 | Frassica et al. | |
| 5,530,238 A | 6/1996 | Meulenbrugge et al. | |
| 5,533,496 A | 7/1996 | De Faria-Correa et al. | |
| 5,536,236 A | 7/1996 | Yabe et al. | |
| 5,556,367 A | 9/1996 | Yabe et al. | |
| 5,613,936 A | 3/1997 | Czarnek et al. | |
| 5,614,943 A | 3/1997 | Nakamura et al. | |
| 5,626,553 A | 5/1997 | Frassica et al. | |
| 5,634,466 A * | 6/1997 | Gruner | 600/459 |
| 5,653,677 A | 8/1997 | Okada et al. | |
| 5,667,476 A | 9/1997 | Frassica et al. | |
| 5,679,216 A | 10/1997 | Takayama et al. | |
| 5,681,260 A | 10/1997 | Ueda et al. | |
| 5,682,199 A * | 10/1997 | Lankford | 348/72 |
| 5,685,822 A | 11/1997 | Harhen | |
| 5,692,729 A | 12/1997 | Harhen | |
| 5,696,850 A | 12/1997 | Parulski et al. | |
| 5,702,348 A | 12/1997 | Harhen | |
| 5,706,128 A | 1/1998 | Greenberg | |
| 5,722,933 A | 3/1998 | Yabe et al. | |
| 5,752,912 A | 5/1998 | Takahashi et al. | |
| 5,762,603 A | 6/1998 | Thompson | |
| 5,817,061 A | 10/1998 | Goodwin et al. | |
| 5,827,177 A | 10/1998 | Oneda et al. | |
| 5,833,603 A * | 11/1998 | Kovacs et al. | 600/317 |
| 5,843,103 A | 12/1998 | Wulfman | |
| 5,843,460 A | 12/1998 | Labigne et al. | |
| 5,860,914 A | 1/1999 | Chiba et al. | |
| 5,876,329 A | 3/1999 | Harhen | |
| 5,916,147 A | 6/1999 | Boury | |
| 5,924,977 A | 7/1999 | Yabe et al. | |
| 5,982,932 A | 11/1999 | Prokoski | |
| 5,989,182 A | 11/1999 | Hori et al. | |
| 5,989,224 A | 11/1999 | Exline et al. | |
| 6,017,358 A | 1/2000 | Yoon | |
| 6,026,323 A | 2/2000 | Skladnev et al. | |
| 6,066,090 A | 5/2000 | Yoon | |
| 6,071,233 A * | 6/2000 | Ishikawa et al. | 600/104 |
| 6,099,464 A | 8/2000 | Shimizu et al. | |
| 6,099,466 A | 8/2000 | Sano et al. | |
| 6,099,485 A | 8/2000 | Patterson | |
| 6,106,463 A | 8/2000 | Wilk | |
| 6,174,280 B1 | 1/2001 | Oneda et al. | |
| 6,190,330 B1 | 2/2001 | Harhen | |
| 6,214,028 B1 | 4/2001 | Yoon et al. | |
| 6,261,226 B1 | 7/2001 | McKenna et al. | |
| 6,261,307 B1 | 7/2001 | Yoon et al. | |
| 6,277,064 B1 | 8/2001 | Yoon | |
| 6,296,608 B1 | 10/2001 | Daniels et al. | |
| 6,301,047 B1 | 10/2001 | Hoshino et al. | |
| 6,350,231 B1 | 2/2002 | Ailinger et al. | |
| 6,369,855 B1 | 4/2002 | Chauvel et al. | |
| 6,375,653 B1 | 4/2002 | Desai | |
| 6,387,043 B1 | 5/2002 | Yoon | |
| 6,433,492 B1 | 8/2002 | Buonavita | |
| 6,456,684 B1 | 9/2002 | Mun et al. | |
| 6,461,294 B1 | 10/2002 | Oneda et al. | |
| 6,482,149 B1 | 11/2002 | Torii | |
| 6,527,704 B1 | 3/2003 | Chang et al. | |
| 6,547,724 B1 | 4/2003 | Soble et al. | |
| 6,554,767 B2 * | 4/2003 | Tanaka | 600/175 |
| 6,564,088 B1 | 5/2003 | Soller et al. | |
| 6,640,017 B1 | 10/2003 | Tsai et al. | |
| 6,648,816 B2 | 11/2003 | Irion et al. | |
| 6,683,716 B1 | 1/2004 | Costales | |
| 6,687,010 B1 * | 2/2004 | Horii et al. | 356/479 |
| 6,697,536 B1 | 2/2004 | Yamada | |
| 6,699,180 B2 | 3/2004 | Kobayashi | |
| 6,736,773 B2 * | 5/2004 | Wendlandt et al. | 600/173 |
| 6,748,975 B2 | 6/2004 | Hartshorne et al. | |
| 6,796,939 B1 * | 9/2004 | Hirata et al. | 600/179 |
| 6,833,871 B1 | 12/2004 | Merrill et al. | |
| 6,845,190 B1 | 1/2005 | Smithwick et al. | |
| 6,891,977 B2 | 5/2005 | Gallagher | |
| 6,916,286 B2 | 7/2005 | Kazakevich | |
| 6,929,636 B1 | 8/2005 | von Alten | |
| 6,951,536 B2 | 10/2005 | Yokoi et al. | |
| 6,965,702 B2 | 11/2005 | Gallagher | |
| 6,966,906 B2 | 11/2005 | Brown | |
| 6,974,411 B2 | 12/2005 | Belson | |
| 6,997,871 B2 | 2/2006 | Sonnenschein | |
| 7,004,900 B2 | 2/2006 | Wendlandt et al. | |
| 7,029,435 B2 | 4/2006 | Nakao | |
| 7,041,050 B1 | 5/2006 | Ronald | |
| 7,095,548 B1 | 8/2006 | Cho et al. | |
| 7,103,228 B2 | 9/2006 | Kraft et al. | |
| 7,116,352 B2 | 10/2006 | Yaron | |
| 7,173,656 B1 | 2/2007 | Dunton et al. | |

| | | |
|---|---|---|
| 7,228,004 B2 | 6/2007 | Gallagher et al. |
| 7,280,141 B1 | 10/2007 | Frank et al. |
| 7,322,934 B2 | 1/2008 | Miyake et al. |
| 7,341,555 B2 | 3/2008 | Ootawara et al. |
| 7,362,911 B1 | 4/2008 | Frank |
| 7,435,218 B2 * | 10/2008 | Krattiger et al. ............... 600/175 |
| 7,436,562 B2 * | 10/2008 | Nagasawa et al. ......... 359/196.1 |
| 7,507,200 B2 | 3/2009 | Okada |
| 7,551,196 B2 | 6/2009 | Ono et al. |
| 7,556,599 B2 * | 7/2009 | Rovegno ........................ 600/175 |
| 7,561,190 B2 | 7/2009 | Deng et al. |
| 7,621,869 B2 | 11/2009 | Ratnakar |
| 7,646,520 B2 * | 1/2010 | Funaki et al. ............... 359/205.1 |
| 7,678,043 B2 * | 3/2010 | Gilad ............................ 600/109 |
| 7,683,926 B2 | 3/2010 | Schechterman et al. |
| 7,749,156 B2 | 7/2010 | Ouchi |
| 7,825,964 B2 | 11/2010 | Hoshino et al. |
| 7,927,272 B2 | 4/2011 | Bayer et al. |
| 8,064,666 B2 | 11/2011 | Bayer |
| 2001/0007468 A1 | 7/2001 | Sugimoto et al. |
| 2001/0037052 A1 | 11/2001 | Higuchi et al. |
| 2001/0051766 A1 | 12/2001 | Gazdinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0193662 A1 | 12/2002 | Belson |
| 2003/0004399 A1 | 1/2003 | Belson |
| 2003/0011768 A1 | 1/2003 | Jung et al. |
| 2003/0032863 A1 | 2/2003 | Kazakevich |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0130711 A1 | 7/2003 | Pearson et al. |
| 2003/0153866 A1 | 8/2003 | Long et al. |
| 2003/0161544 A1 | 8/2003 | Gallagher |
| 2003/0171650 A1 | 9/2003 | Tartaglia et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197793 A1 | 10/2003 | Mitsunaga et al. |
| 2003/0225433 A1 | 12/2003 | Nakao |
| 2003/0233115 A1 | 12/2003 | Eversull et al. |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0097790 A1 | 5/2004 | Farkas et al. |
| 2004/0109164 A1 | 6/2004 | Horii et al. |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0207618 A1 | 10/2004 | Williams et al. |
| 2004/0242987 A1 | 12/2004 | Liew et al. |
| 2005/0010084 A1 | 1/2005 | Tsai |
| 2005/0014996 A1 * | 1/2005 | Konomura et al. ........... 600/175 |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 * | 8/2005 | Mackin ........................ 600/120 |
| 2005/0203420 A1 | 9/2005 | Kleen et al. |
| 2005/0215911 A1 | 9/2005 | Alfano et al. |
| 2005/0222500 A1 | 10/2005 | Itoi |
| 2005/0228224 A1 | 10/2005 | Okada et al. |
| 2005/0267361 A1 * | 12/2005 | Younker et al. ............... 600/423 |
| 2005/0272975 A1 | 12/2005 | McWeeney et al. |
| 2005/0272977 A1 | 12/2005 | Saadat et al. |
| 2006/0022234 A1 * | 2/2006 | Adair et al. .................... 257/292 |
| 2006/0004267 A1 | 3/2006 | Xie et al. |
| 2006/0052709 A1 | 3/2006 | DeBaryshe et al. |
| 2006/0058584 A1 * | 3/2006 | Hirata ........................ 600/179 |
| 2006/0106286 A1 | 5/2006 | Wendlandt et al. |
| 2006/0149127 A1 | 7/2006 | Seddiqui et al. |
| 2006/0149129 A1 * | 7/2006 | Watts et al. .................... 600/113 |
| 2006/0183975 A1 | 8/2006 | Saadat et al. |
| 2006/0217594 A1 * | 9/2006 | Ferguson ........................ 600/175 |
| 2006/0279632 A1 | 12/2006 | Anderson |
| 2006/0285766 A1 | 12/2006 | Ali |
| 2006/0293562 A1 | 12/2006 | Uchimura et al. |
| 2007/0015989 A1 | 1/2007 | Desai et al. |
| 2007/0083081 A1 | 4/2007 | Schlagenhauf et al. |
| 2007/0103460 A1 | 5/2007 | Zhang et al. |
| 2007/0142711 A1 | 6/2007 | Bayer et al. |
| 2007/0173686 A1 * | 7/2007 | Lin et al. ........................ 600/102 |
| 2007/0177009 A1 | 8/2007 | Bayer et al. |
| 2007/0183685 A1 | 8/2007 | Wada et al. |
| 2007/0185384 A1 | 8/2007 | Bayer et al. |
| 2007/0225552 A1 * | 9/2007 | Segawa et al. ................. 600/102 |
| 2007/0238927 A1 * | 10/2007 | Ueno et al. .................... 600/145 |
| 2007/0244354 A1 | 10/2007 | Bayer |
| 2007/0270642 A1 | 11/2007 | Bayer et al. |
| 2007/0279486 A1 | 12/2007 | Bayer et al. |
| 2007/0280669 A1 | 12/2007 | Karim |
| 2007/0293720 A1 | 12/2007 | Bayer |
| 2008/0021274 A1 | 1/2008 | Bayer et al. |
| 2008/0033450 A1 | 2/2008 | Bayer et al. |
| 2008/0039693 A1 * | 2/2008 | Karasawa ....................... 600/175 |
| 2008/0079827 A1 | 4/2008 | Hoshino et al. |
| 2008/0097292 A1 | 4/2008 | Cabiri |
| 2008/0130108 A1 | 6/2008 | Bayer et al. |
| 2008/0199829 A1 | 8/2008 | Paley et al. |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0036739 A1 | 2/2009 | Hadani |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0213211 A1 | 8/2009 | Bayer et al. |
| 2009/0231419 A1 | 9/2009 | Bayer et al. |
| 2010/0217076 A1 * | 8/2010 | Ratnakar ........................ 600/104 |
| 2011/0160535 A1 | 6/2011 | Bayer et al. |

FOREIGN PATENT DOCUMENTS

| | | |
|---|---|---|
| DE | 196 26433 | 1/1998 |
| DE | 19626433 A1 | 1/1998 |
| DE | 20 2006 017 173 U1 | 3/2007 |
| EP | 0 586 162 | 3/1994 |
| EP | 1 570 778 A1 | 9/2005 |
| EP | 1 769 720 A1 | 4/2007 |
| FR | 711 949 | 9/1931 |
| JP | 49-130235 A | 12/1974 |
| JP | 56-9712 | 1/1981 |
| JP | 62-094312 U1 | 6/1987 |
| JP | 63-309912 A | 12/1988 |
| JP | 3-159629 A | 7/1991 |
| JP | 5-341210 A | 12/1993 |
| JP | 6-130308 A | 5/1994 |
| JP | 7-352 A | 1/1995 |
| JP | 7-354 A | 1/1995 |
| JP | 7-21001 U | 4/1995 |
| JP | 8-206061 A | 8/1996 |
| JP | 7-136108 A | 5/1998 |
| JP | 11-76150 A | 3/1999 |

| | | |
|---|---|---|
| WO | WO 93/15648 | 8/1993 |
| WO | WO-99/17542 A1 | 4/1999 |
| WO | WO-99/30506 A1 | 6/1999 |
| WO | WO 02/085194 | 10/2002 |
| WO | WO-02085194 A1 | 10/2002 |
| WO | WO-02/094105 A2 | 11/2002 |
| WO | WO-02/094105 A3 | 11/2002 |
| WO | WO-2006/073676 A1 | 7/2006 |
| WO | WO-2006/073725 A1 | 7/2006 |
| WO | WO-2006/073725 A1 | 7/2006 |
| WO | WO-2006/110275 A2 | 10/2006 |
| WO | WO-2006/110275 A3 | 10/2006 |
| WO | WO-2007/015241 A2 | 2/2007 |
| WO | WO-2007070644 A2 | 6/2007 |
| WO | WO-2007087421 A2 | 8/2007 |
| WO | WO-2007092533 A2 | 8/2007 |
| WO | WO-2007092636 A2 | 8/2007 |
| WO | WO-2007/136859 A2 | 11/2007 |
| WO | WO-2007/136859 A3 | 11/2007 |
| WO | WO-2007/136879 A2 | 11/2007 |
| WO | WO-2007/136879 A3 | 11/2007 |
| WO | WO-2007/136879 B1 | 11/2007 |
| WO | WO-2009/014895 A1 | 1/2009 |
| WO | WO-2009/015396 A2 | 1/2009 |
| WO | WO-2009/049322 A2 | 4/2009 |
| WO | WO-2009/049322 A3 | 4/2009 |
| WO | WO-2009062179 A1 | 5/2009 |

OTHER PUBLICATIONS

Invitation to Pay Additional Fees for PCT/US2008/071390, filed Jul. 28, 2008, mailed Nov. 11, 2008, 5 pgs.
U.S. Appl. No. 11/153,007, filed Jun. 14, 2005, Seddiqui et al.
U.S. Appl. No. 11/160,646, filed Jul. 1, 2005, Desai et al.
U.S. Appl. No. 11/215,660, filed Aug. 29, 2005, Watts et al.
U.S. Appl. No. 11/626,189, filed Jan. 23, 2007, Bayer et al.
U.S. Appl. No. 11/673,470, filed Feb. 9, 2007, Bayer et al.
U.S. Appl. No. 11/672,020, filed Feb. 6, 2007, Bayer et al.
U.S. Appl. No. 11/736,438, filed Apr. 17, 2007, Bayer.
U.S. Appl. No. 11/751,596, filed May 21, 2007, Bayer.
U.S. Appl. No. 11/751,597, filed May 21, 2007, Bayer et al.
U.S. Appl. No. 11/751,605, filed May 21, 2007, Diel et al.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
U.S. Appl. No. 11/828,835, filed Jun. 14, 2005, Bayer.
U.S. Appl. No. 11/834,540, filed Aug. 6, 2007, Bayer.
Invitation to Pay Additional Fees for PCT/US2007/002096, filed Jan. 23, 2007, mailed Jul. 6, 2007, 4 pgs.
Invitation to Pay Additional Fees for PCT/US2007/003631, filed Feb. 9, 2007, mailed Aug. 7, 2007, 5 pgs.
Invitation to Pay Additional Fees for PCT/US2007/003322, filed Feb. 6, 2007, mailed Aug. 7, 2007, 6 pgs.
"European Application Serial No. 06845440.4, Office Action mailed Feb. 5, 2010", 4 pgs.
"European Application Serial No. 07717235.1, Office Action mailed Apr. 1, 2010", 2 pgs.
"European Application Serial No. 07763368.3, Office Action mailed May 5, 2009", 3 pgs.
"European Application Serial No. 07763368.3, Response filed Nov. 11, 2009 to Office Action mailed May 5, 2009", 10 pgs.
"International Application Serial No. PCT/US2006/047748, Search Report mailed Jun. 20, 2007", 3 pgs.
"International Application Serial No. PCT/US2007/003631 International Search Report mailed Oct. 26, 2007", 3 pgs.
"International Application Serial No. PCT/US2007/003631 Written Opinion mailed Oct. 26, 2007", 7 pgs.
"International Application Serial No. PCT/US2008/083034, Search Report mailed May 10, 2010", 3 pgs.
"International Application Serial No. PCT/US2008/083034, Written Opinion mailed May 10, 2010", 4 pgs.
"U.S. Appl. No. 11/215,660, Final Office Action mailed Nov. 1, 2010", 12 pgs.
"U.S. Appl. No. 11/215,660, Final Office Action mailed Oct. 8, 2009", 12 pgs.
"U.S. Appl. No. 11/215,660, Non Final Office Action mailed Mar. 25, 2009", 11 pgs.
"U.S. Appl. No. 11/215,660, Non-Final Office Action mailed Mar. 29, 2010", 16 pgs.
"U.S. Appl. No. 11/215,660, Response filed Jan. 26, 2009 to Restriction Requirement mailed Oct. 30, 2008", 2 pgs.
"U.S. Appl. No. 11/215,660, Response filed Mar. 8, 2010 to Final Office Action mailed Oct. 8, 2009", 11 pgs.
"U.S. Appl. No. 11/215,660, Response filed Jun. 29, 2009 to Non Final Office Action mailed Mar. 25, 2009", 9 pgs.
"U.S. Appl. No. 11/215,660, Response filed Aug. 30, 2010 to Non Final Office Action mailed Mar. 29, 2010", 17 pgs.
"U.S. Appl. No. 11/215,660, Restriction Requirement mailed Oct. 30, 2008", 7 pgs.
"U.S. Appl. No. 11/626,189, Non-Final Office Action mailed Oct. 18, 2010", 12 pgs.
"U.S. Appl. No. 11/626,189, Response filed Sep. 9, 2010 to Restriction Requirement mailed Aug. 10, 2010", 8 pgs.
"U.S. Appl. No. 11/626,189, Restriction Requirement mailed Aug. 10, 2010", 5 pgs.
"U.S. Appl. No. 11/672,020, Preliminary Amendment filed Jan. 26, 2009", 11 pgs.
"U.S. Appl. No. 11/672,020, Substitute Preliminary Amendment filed Mar. 8, 2010", 2 pgs.
"U.S. Appl. No. 11/751,605, Response filed Jul. 23, 2010 to Restriction Requirement mailed Jun. 25, 2010", 9 pgs.
"U.S. Appl. No. 11/751,605, Restriction Requirement mailed Jun. 25, 2010", 9 pgs.
"U.S. Appl. No. 11/828,835, Non-Final Office Action mailed Oct. 28, 2010", 11 pgs.
"U.S. Appl. No. 11/828,835, Response filed Oct. 21, 2010 to Restriction Requirement mailed Sep. 21, 2010", 7 pgs.
"U.S. Appl. No. 11/828,835, Restriction Requirement mailed Sep. 21, 2010", 6 pgs.
"European Application Serial No. 06845440.4, Office Action Response filed Jul. 8, 2010", 16 pgs.
"European Application Serial No. 07717235.1, Office Action Response Filed—Aug. 18, 2010", 5 pgs.
"International Application Serial No. PCT/US2005/045499, Search Report mailed May 18, 2006", 4 pgs.
"U.S. Appl. No. 11/215,660, Response filed Feb. 28, 2011 to Final Office Action mailed Nov. 1, 2010", 11 pgs.
"U.S. Appl. No. 11/626,189, Response filed Apr. 12, 2011 to Non Final Office Action mailed Oct. 18, 2010", 18 pgs.
"U.S. Appl. No. 11/751,605, Final Office Action mailed Apr. 29, 2011", 9 pgs.
"U.S. Appl. No. 11/751,605, Non Final Office Action mailed Dec. 22, 2010", 11 pgs.
"U.S. Appl. No. 11/751,605, Response filed Feb. 25, 2011 to Non Final Office Action mailed Dec. 22, 2010", 15 pgs.
"U.S. Appl. No. 11/828,835, Final Office Action mailed Mar. 22, 2011", 12 pgs.
"U.S. Appl. No. 11/828,835, Response filed Feb. 9, 2011 to Non Final Office Action mailed Oct. 28, 2010", 10 pgs.
Advisory Action mailed on May 23, 2011, for U.S. Appl. No. 11/751,605, filed May 21, 2007, 3 pages.
Amendment in Response to Non-Final Office Action filed on Oct. 22, 2010, for U.S. Appl. No. 11/834,540, filed Aug. 6, 2007, 13 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in Response to Non-Final Office Action filed on May 24, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in response to Final Office Action filed on Jun. 7, 2011, for U.S. Appl. No. 11/751,605, filed May 21, 2007, 11 pages.
Amendment in Response to Final Office Action filed on Dec. 7, 2011, for U.S. Appl. No. 11/736,438, filed Apr. 17, 2007, 10 pages.

European Communication mailed on Jan. 22, 2009, for European Application No. 07777255.6, filed on May 21, 2007, 2 pages.
European Office Action mailed on Nov. 8, 2010, for European Patent Application No. 05854262.2, filed on Dec. 8, 2005, 5 pages.
European Office Action mailed on Jun. 14, 2011, for European Patent Application No. 07795177.0, filed on May 21, 2007, 6 pages.
Final Office Action mailed on Aug. 3, 2011, for U.S. Appl. No. 11/736,438, filed Apr. 17, 2007, 11 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Dec. 11, 2007, for PCT Patent Application No. PCT/US2007/012358, filed on May 21, 2007, 3 pages.
International Search Report mailed on Jan. 28, 2008, for PCT Patent Application No. PCT/US2007/012189, filed on May 21, 2007, 2 pages.
International Search Report mailed on Feb. 25, 2009, for PCT Patent Application No. PCT/US2008/071390, filed on Jul. 28, 2008, 2 pages.
International Search Report mailed on Apr. 6, 2009, for PCT Patent Application No. PCT/US2008/079878, filed on Oct. 14, 2008, 3 pages.
Invitation to Pay Additional Fees mailed on Dec. 29, 2008, for PCT Patent Application No. PCT/US2008/079891, filed on Oct. 14, 2008, 7 pages.
Japanese Office Action mailed on Jul. 19, 2011, for Japanese Patent Application No. 2007-550378, filed on Dec. 8, 2005, with English Translation, 11 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Aug. 24, 2010, for U.S. Appl. No. 11/834,540, filed Aug. 6, 2007, 11 pages.
Non-Final Office Action mailed on Mar. 2, 2011, for U.S. Appl. No. 11/736,438, filed Apr. 17, 2007, 10 pages.
Non-Final Office Action mailed on May 23, 2011, for U.S. Appl. No. 12/101,050, filed Apr. 10, 2008, 11 pages.
Non-Final Office Action mailed on Jun. 28, 2011, for U.S. Appl. No. 11/938,256, filed Nov. 10, 2007, 23 pages.
Non-Final Office Action mailed on Aug. 15, 2011, for U.S. Appl. No. 11/626,189, filed Jan. 23, 2007, 13 pages.
Non-Final Office Action mailed on Aug. 18, 2011, for U.S. Appl. No. 11/751,597, filed May 21, 2007, 25 pages.
Non-Final Office Action mailed on Sep. 9, 2011, for U.S. Appl. No. 11/751,596, filed May 21, 2007, 6 pages.
Non-Final Office Action mailed on Oct. 21, 2011, for PCT U.S. Appl. No. 12/251,406, filed Oct. 14, 2008, 8 pages.
Non-Final Office Action mailed on Oct. 26, 2011, for U.S. Appl. No. 11/673,470, filed Feb. 9, 2007, 40 pages.
Non-Final Office Action mailed on Nov. 23, 2011, for U.S. Appl. No. 11/672,020, filed Feb. 6, 2007, 12 pages.
Notice of Allowance mailed on Dec. 13, 2010, for U.S. Appl. No. 11/834,540, filed Aug. 6, 2007, 4 pages.
Notice of Allowance mailed on Jul. 22, 2011, for U.S. Appl. No. 12/101,050, filed Apr. 10, 2008, 7 pages.
Response to European Communication filed Feb. 6, 2009, for European Patent Application No. 07777255.6, filed on May 21, 2007, 5 pages.
Response to European Office Action filed on Mar. 8, 2011, for European Patent Application No. 05854262.2, filed on Dec. 8, 2005, 11 pages.
Response to Restriction Requirement filed on Aug. 4, 2010, for U.S. Appl. No. 11/834,540, filed Aug. 6, 2007, 5 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 11 pages.
Response to Restriction Requirement filed on Jun. 16, 2011, for U.S. Appl. No. 11/751,596, filed May 21, 2007, 8 pages.
Response to Restriction Requirement filed on Oct. 31, 2011, for U.S. Appl. No. 11/672,020, filed Feb. 6, 2007, 3 pages.
Restriction Requirement mailed on Jul. 13, 2010, for U.S. Appl. No. 11/834,540, filed Aug. 6, 2007, 8 pages.
Restriction Requirement mailed on Dec. 10, 2010, for U.S. Appl. No. 11/736,438, filed Apr. 17, 2007, 16 pages.
Restriction Requirement mailed on Mar. 11, 2011, for U.S. Appl. No. 12/101,050, filed Apr. 10, 2008, 6 pages.
Restriction Requirement mailed on Jun. 6, 2011, for U.S. Appl. No. 11/751,596, filed May 21, 2007, 6 pages.
Restriction Requirement mailed on Sep. 29, 2011, for U.S. Appl. No. 11/672,020, filed Feb. 6, 2007, 6 pages.
Restriction Requirement mailed on Nov. 28, 2011, for U.S. Appl. No. 12/251,383, filed Oct. 14, 2008, 6 pages.
Written Opinion of the International Searching Authority mailed on May 18, 2006, for PCT Patent Application No. PCT/US2005/045499, filed on Dec. 8, 2005, 9 pages.
Written Opinion of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096 filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages.
Written Opinion of the International Searching Authority mailed on Dec. 11, 2007, for PCT Patent Application No. PCT/US2007/012358, filed on May 21, 2007, 6 pages.
Written Opinion of the International Searching Authority mailed on Jan. 28, 2008, for PCT Patent Application No. PCT/US2007/012189, filed on May 21, 2007, 7 pages.
Written Opinion of the International Searching Authority mailed on Oct. 23, 2008, for PCT Patent Application No. PCT/US2008/069435, filed on Jul. 8, 2008, 6 pages.
Written Opinion of the International Searching Authority mailed on Feb. 25, 2009, for PCT Patent Application No. PCT/US2008/071390, filed on Jul. 28, 2008, 7 pages.
Written Opinion of International Searching Authority mailed on Mar. 13, 2009, for PCT Patent Application No. PCT/US2008/079891, filed on Nov. 10, 2008, 5 pages.
Written Opinion of International Searching Authority mailed on Apr. 6, 2009, for PCT Patent Application No. PCT/US2008/079878, filed on Oct. 14, 2008, 13 pages.
International Search Report mailed on Mar. 13, 2009, for PCT Patent Application No. PCT/US2008/079891, filed on Nov. 10, 2008, 2 pages.

* cited by examiner

ENDOSCOPE HAVING DETACHABLE IMAGING DEVICE AND METHOD OF USING

This application claims the benefit of U.S. Provisional Patent Application No. 60/750,325, filed Dec. 13, 2005, the entire disclosure of which is incorporated herein by reference.

This application also claims the benefit of U.S. Provisional Patent Application No. 60/761,475, filed Jan. 23, 2006, the entire disclosure of which is incorporated herein by reference.

This application also claims the benefit of U.S. Provisional Patent Application No. 60/772,442, filed Feb. 9, 2006, the entire disclosure of which is incorporated herein by reference.

This application further claims the benefit of U.S. Provisional Patent Application No. 60/802,056, filed May 19, 2006, the entire disclosure of which is incorporated herein by reference.

The entire disclosure of U.S. patent application Ser. No. 11/215,660, filed Aug. 29, 2005, is incorporated herein by reference.

TECHNICAL FIELD OF THE INVENTION

The present invention relates to a detachable imaging device, an endoscope having a detachable imaging device, and a method of configuring an endoscope with a detachable imaging device.

BACKGROUND OF THE INVENTION

An endoscope is a medical device comprising a flexible tube and a camera mounted on the distal end of the tube. The endoscope is insertable into an internal body cavity through a body orifice to examine the body cavity and tissues for diagnosis. The tube of the endoscope has one or more longitudinal channels, through which an instrument can reach the body cavity to take samples of suspicious tissues or to perform other surgical procedures such as polypectomy.

There are many types of endoscopes, and they are named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

Each endoscope has a single forward viewing camera mounted at the distal end of the endoscope to transmit an image to an eyepiece or video camera at the proximal end. The camera is used to assist a medical professional in advancing the endoscope into a body cavity and looking for abnormalities. The camera provides the medical professional with a two-dimensional view from the distal end of the endoscope. To capture an image from a different angle or in a different portion, the endoscope must be repositioned or moved back and forth. Repositioning and movement of the endoscope prolongs the procedure and causes added discomfort, complications, and risks to the patient. Additionally, in an environment similar to the lower gastro-intestinal tract, flexures, tissue folds and unusual geometries of the organ may prevent the endoscope's camera from viewing all areas of the organ. The unseen area may cause a potentially malignant (cancerous) polyp to be missed.

This problem can be overcome by providing an auxiliary camera, which presents an image of the areas not viewable by the endoscope's main camera. The auxiliary camera can be oriented backwards to face the main camera. This arrangement of cameras can provide both front and rear views of an area or an abnormality. In the case of polypectomy where a polyp is excised by placing a wire loop around the base of the polyp, the camera arrangement allows better placement of the wire loop to minimize damage to the adjacent healthy tissue.

Unfortunately, most of the endoscopes currently in use do not have such an auxiliary camera. To replace these existing endoscopes with new endoscopes with auxiliary cameras is expensive. Therefore, it is desirable to provide the existing endoscopes with retrofit auxiliary cameras. Additionally, to avoid the costs of modifying existing endoscopes, it is desirable to provide retrofit auxiliary cameras that do not require significant modification of the existing endoscopes.

Although a channel of an endoscope can be used to accommodate an auxiliary camera that does not require modification of the endoscope, the loss of a channel may impair the endoscope's ability to perform all of its designed functions. Thus the ability of the retrofit auxiliary camera to function without using an endoscope channel is desirable.

SUMMARY OF THE INVENTION

According to some aspects of the present invention, a retrofit auxiliary camera is provided that does not require significant modification of an existing endoscope or use of a channel of the endoscope, thereby avoiding the costs of modifying the endoscope and preserving all of the endoscope's designed functions.

In accordance with one aspect of the invention, a detachable imaging device can be attached to a distal end region of an endoscope's insertion tube. The detachable imaging device includes an attachment that can detachably attach the imaging device to the distal end region of the endoscope's insertion tube. The detachable imaging device includes also a wireless imaging element connected to the attachment.

In accordance with another aspect of the invention, an endoscope includes a detachable imaging device and an insertion tube having a distal end region. The detachable imaging device includes an attachment that detachably attaches the detachable imaging device to the distal end region of the insertion tube, and a wireless imaging element connected to the attachment.

In accordance with a further aspect of the invention, a method of configuring an endoscope includes attaching an attachment of a detachable imaging device of an endoscope to a distal end region of the insertion tube of the endoscope.

In accordance with one embodiment of the invention, the attachment includes a ring. Preferably, the ring has an inner diameter that is designed to provide a friction fit between the inner surface of the ring and a cylindrical outer surface of the distal end region of the insertion tube of the endoscope. The inner diameter of the ring may be slightly smaller than the outer diameter of the distal end region of the insertion tube to provide the friction fit. Also the inner surface of the ring may include a rubber or silicon surface.

In accordance with another embodiment of the invention, the detachable imaging device includes a link that connects the imaging device to the attachment. Preferably, the link is flexible.

In accordance with yet another embodiment of the invention, the detachable imaging device includes an external control box that is configured to adjust parameters of the wireless imaging element.

In accordance with another embodiment of the invention, the detachable imaging device includes an external control box that is configured to send images from the wireless imaging element to a patient records database.

In accordance with still another embodiment of the invention, the detachable imaging device includes a support mechanism that increases the rigidity of the detachable imaging device and reduces the bending of the link.

In accordance with yet still another embodiment of the invention, the wireless imaging element includes an imaging unit and/or a light source. The imaging unit may be mounted on the proximal end of the wireless imaging element and faces towards a main imaging device mounted on the distal end of the insertion tube. Preferably, the imaging unit and the main imaging device provide different views of the same area. To reduce light interference, the imaging element and the main imaging device and their light sources may be turned on and off alternately. Preferably the imaging element and the main imaging device and their light sources are turned on and off at a sufficiently high frequency that the eyes do not sense that the imaging element and the main imaging device and their light sources are intermittently turned on and off.

The wireless imaging element may include another imaging unit, which is mounted on the distal end of the wireless imaging element and faces in the same direction as the main imaging device. The wireless imaging element may also include another light source, which is mounted on the distal end of the wireless imaging element and faces in the same direction as the main imaging device.

In accordance with a further embodiment of the invention, the wireless imaging element includes a channel aligned with a channel of the insertion tube. This channel of the wireless imaging element may extend from the proximal end of the wireless imaging element to the distal end of the wireless imaging element.

In accordance with a still further embodiment of the invention, the wireless imaging element includes a housing that is used to accommodate the wireless imaging unit. Preferably, the housing includes two housing elements that sealingly form the housing.

In accordance with a yet still further embodiment of the invention, the detachable imaging device includes a link that connects the imaging device to the attachment. Preferably, the link, attachment, and one of the housing elements form a unitary unit.

In accordance with another embodiment of the invention, the wireless imaging element is accommodated within the attachment. In some embodiments, the detachable imaging device includes two or more wireless imaging elements, and the wireless imaging elements are mounted on at least one of the distal end, proximal end and side of the attachment.

Although certain aspects of the present invention have been discussed so far in terms of a retrofit auxiliary imaging device, it should be emphasized that the present invention is not limited to a retrofit auxiliary imaging device. On the contrary, a detachable imaging device of the present invention may be manufactured as an original part of an endoscope. If the detachable imaging device is needed to provide a rear or retrograde view of an abnormality, the detachable imaging device is installed on the end region of the insertion tube. Alternatively, if the detachable imaging device is not needed, the endoscope can be used without the detachable imaging device.

DETAILED DESCRIPTION OF EMBODIMENTS OF THE INVENTION

Figure 1:
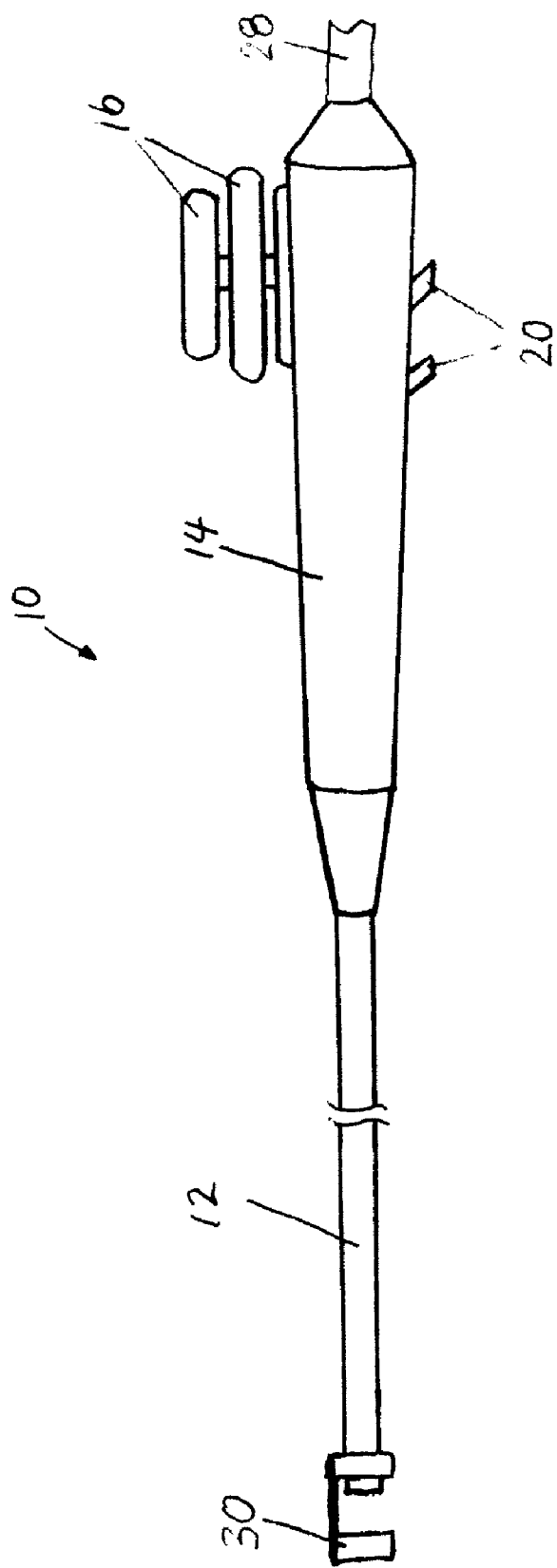
FIG. 1 shows an endoscope according to one embodiment of the present invention.

FIG. 1 illustrates an exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

As shown in FIG. 1, the endoscope 10 may include an insertion tube 12 and a control handle 14 connected to the insertion tube 12. The insertion tube 12 may be detachable from the control handle 14 or may be integrally formed with the control handle 14. The diameter, length and flexibility of the insertion tube 12 depend on the procedure for which the endoscope 10 is used. The insertion tube 12 may be made from or coated with a lubricious material to allow for easy insertion into and easy extraction from a patient.

The control handle 14 may include one or more control knobs 16 that are attached to control cables 18 (FIG. 2) for the manipulation of the insertion tube 12. Preferably, the control cables 18 are symmetrically positioned within the insertion tube 12 and extend along the length of the insertion tube 12. The control cables 18 may be anchored at or near the distal end of the insertion tube 12 such that the rotation of the control knobs 16 moves or bends the insertion tube 12 up and down and/or side to side. In some embodiments, a clutch or breaking component (not shown) may be included with the control knobs 16 to prevent the knobs 16 from being inadvertently rotated such that rotation can only be caused by application of a certain degree of torque to the control knobs 16.

Preferably, the control handle 14 has one or more ports and/or valves. In the embodiment illustrated in FIG. 1, the control handle 14 has two ports and/or valves 20. The ports and/or valves 20 are in communication with their respective channels 22 (FIG. 2) extending through the insertion tube 12. "Y" junctions can be used to designate two ports to a single channel or one port to two channels. The ports and/or valves 20 can be air or water valves, suction valves, instrumentation ports, and suction/instrumentation ports. In some embodiments, one of the channels can be used to supply a washing liquid such as water for washing. A cap (not shown) may be included at the opening of the washing channel to divert the washing liquid onto a lens of an imaging device for cleaning. Another channel may be used to supply a gas, such as $CO_2$ or air into the organ. The channels may also be used to extract fluids or inject fluids, such as a drug in a liquid carrier, into the body. Various biopsy, drug delivery, and other diagnostic and therapeutic devices may also be inserted via the channels to perform specific functions. In some embodiments, various tools may be used with the endoscope 10, such as a retractable needle for drug injection, hydraulically actuated scissors, clamps, grasping tools, electrocoagulation systems, ultrasound transducers, electrical sensors, heating elements, laser mechanisms and other ablation means.

Figure 2:
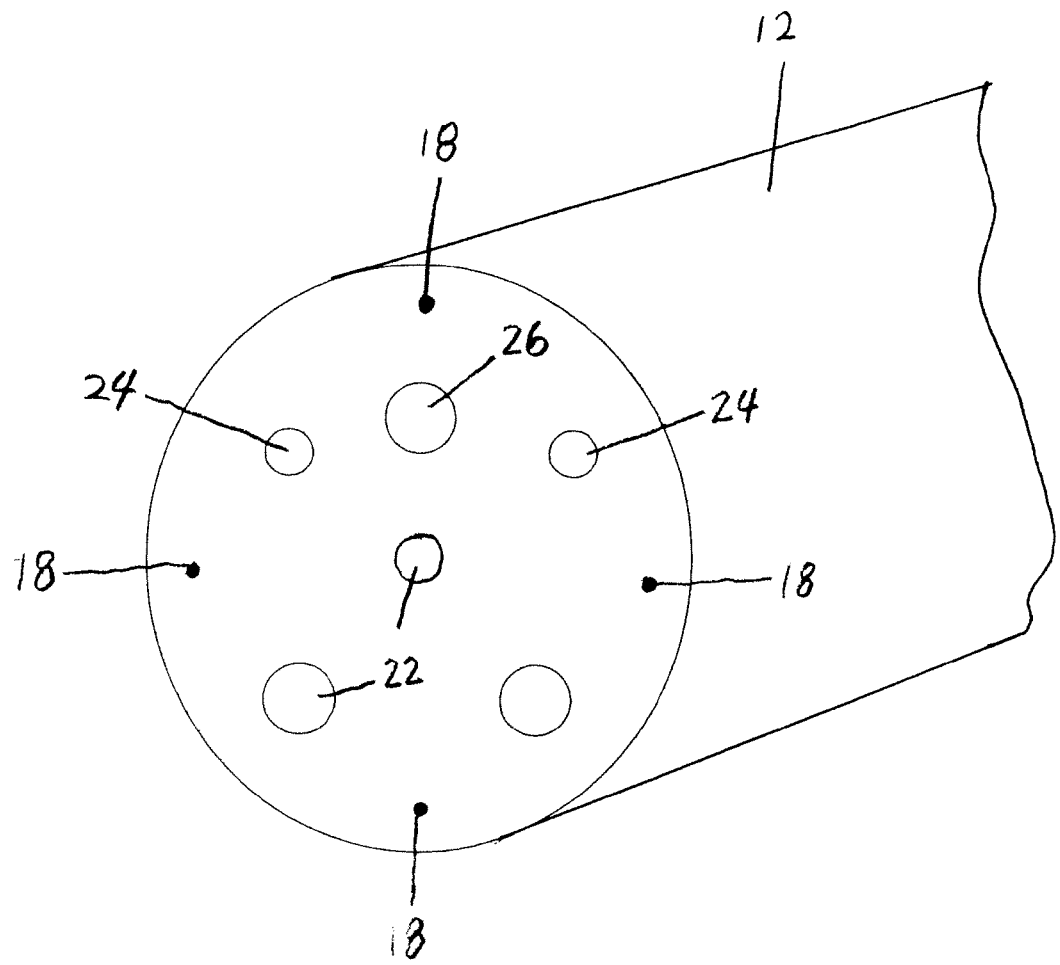
FIG. 2 is a view of the distal end of the insertion tube of the endoscope of FIG. 1.

As illustrated in FIG. 2, the insertion tube 12 may additionally include one or more light sources 24, such as light emitting diodes (LEDs) or fiber optical delivery of light from an external light source, and an imaging device 26. The imaging device 26 may include, for example, a lens, single chip sensor, multiple chip sensor or fiber optic implemented devices. The imaging device 26, in electrical communication with a processor and/or monitor, may provide still images or recorded or live video images. Each light source 24, individually, can be turned on or off. The intensity of each can be adjusted to achieve optimum imaging.

An accessory outlet 28 (FIG. 1) at a proximal end of the control handle 14 provides fluid communication between the air, water and suction channels and the pumps and related accessories. The same outlet or a different outlet can be used for electrical lines to light and imaging components at the distal end of the insertion tube 12.

Figure 3:
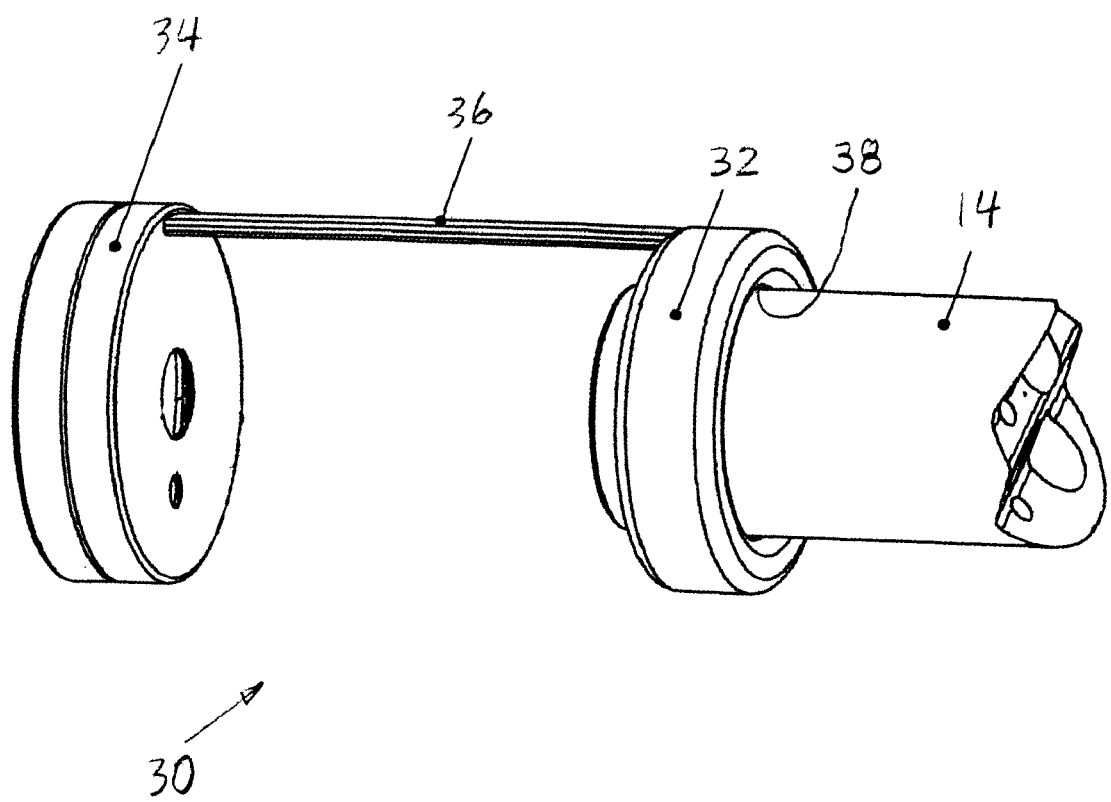
FIG. 3 is a perspective view of a detachable imaging device of the endoscope of FIG. 1.
Figure 4:
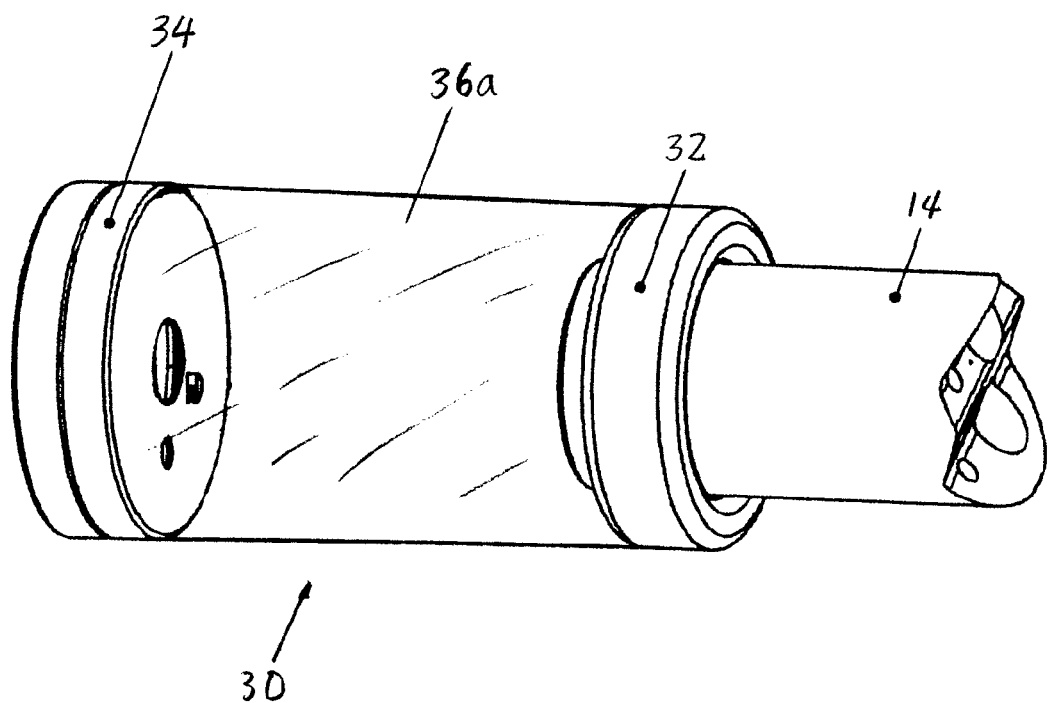
FIG. 4 shows a transparent link connecting the attachment and the imaging element of a detachable imaging device.

As illustrated in FIGS. 1 and 3, the endoscope 10 preferably includes a detachable imaging device 30 attached to the distal end region of the endoscope's insertion tube 14. The detachable imaging device 30 includes an attachment 32 for detachably attaching the imaging device 30 to the distal end region of the insertion tube 14, a wireless imaging element 34, and a link 36 connecting the wireless imaging element 34 to the attachment 32.

Figure 5:
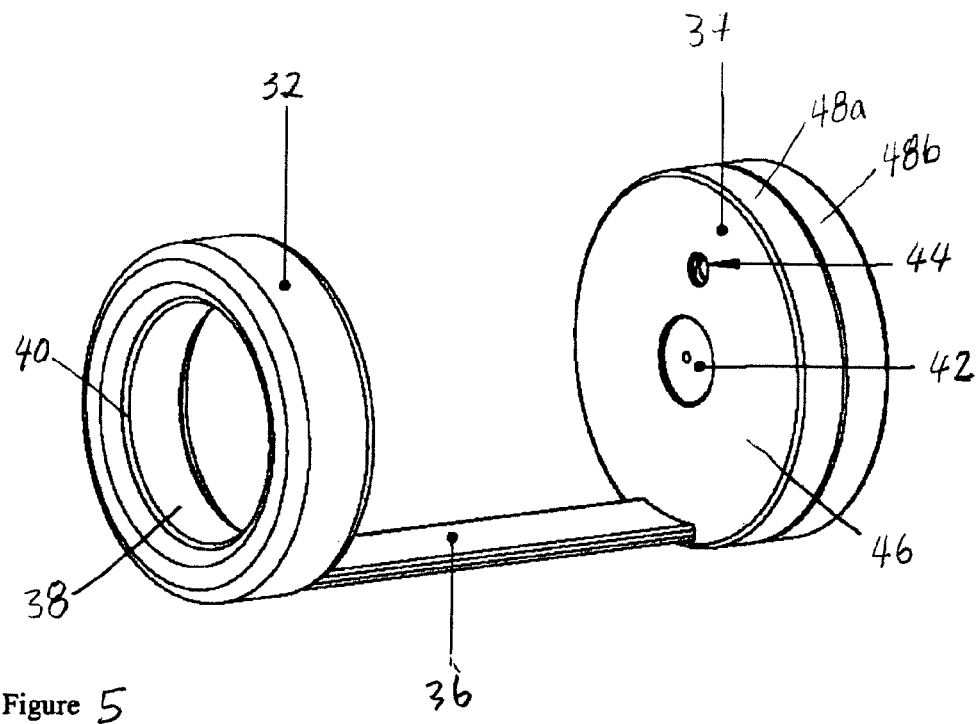
FIG. 5 is another perspective view of the detachable imaging device of FIG. 3.

In this embodiment, which is also shown in FIG. 5, the attachment 32 is configured as a ring. Preferably, the attachment 32 has an inner diameter that is designed to provide a friction fit between the inner surface 38 of the attachment 32 (FIG. 5) and a cylindrical outer surface of the distal end region of the insertion tube 14. This may mean that in the pre-install condition the inner diameter of the attachment 32 is smaller than the outer diameter of the distal end region of the insertion tube 14. When the attachment 32 is slid on the insertion tube 14, the inner surface 38 of the attachment 32 compresses against the outer surface of the insertion tube 14 to provide the friction fit. To secure the attachment 32 on the insertion tube 32, the inner surface 38 of the attachment 32 may include a tacky and/or elastic surface. In some embodiments, this surface may be the surface of a rubber or silicon inner ring 40 (FIG. 5). The rubber or silicon inner ring 40 may be attached to the rest of the attachment 32 by means of an adhesive, welding, mechanical over molding, or snaps. Alternatively, the attachment 32 may be made entirely from rubber or silicon. In general, the attachment can be made from any compressive rubber or polymer or a combination thereof.

Figure 6:
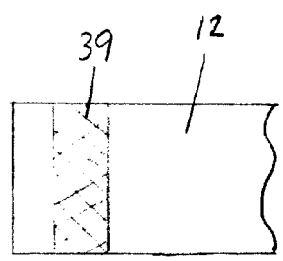
FIG. 6 is a view of a distal end region of the insertion tube having a tacky surface.
Figure 7:
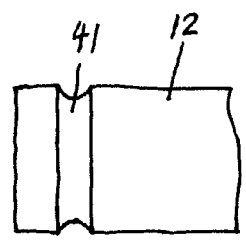
FIG. 7 is a view of a distal end region of the insertion tube having a circular groove.

In some cases such as when the detachable imaging device 30 is made as an original part of the endoscope 10 (i.e., not as a retrofit device), the distal end region of the insertion tube 14 may have one or more features that help retain the detachable imaging device 30. For example, as shown in FIG. 6, the distal end region of the insertion tube 14 may include a tacky surface 39 that engages with the tacky inner surface 38 of the attachment 32 to enhance the friction fit between the attachment 32 and the insertion tube 14. Alternatively or additionally, as shown in FIG. 7, the distal end region of the insertion tube 14 may include a circular groove 41 around the distal end region of the insertion tube 14 for receiving the attachment 32. In general, the distal end region of the insertion tube 14 may include any features that enhance the attachment of the detachable imaging device 30 to the distal end region of the insertion tube 14.

In general, the attachment may be of any suitable configuration that can detachably attach the detachable imaging device 30 to the distal end region of the insertion tube 14. For example, the attachment may be an elastic tube that can be elastically wrapped around the distal end region of the insertion tube 14. Alternatively, the attachment may include one or more screws that can be screwed to attach the imaging device to the distal end region of the insertion tube 14 or unscrewed to detach the imaging device from the distal end region of the insertion tube 14. The attachment may also be similar to the way by which a suction cap for endoscopic mucosal resection is attached to a colonoscope. In general, a suitable attachment may use one or more of, for example, a clamp arrangement, a snap fit, a plastic friction fit, or bonding.

The link 36 connects the imaging device 34 to the attachment 32. In the illustrated embodiment, the link 36 is a generally elongated, flat, straight bar, although the link may be configured in any suitable manner. For example, the link may be curved and may have a circular or square cross-section. The link may comprise one pole, as shown in FIG. 3, or two or more poles to enhance support to the imaging element 34. In some embodiments, the link may be made from a transparent material, and as shown in FIG. 5 the transparent link may be a transparent tube 36a connected to the circumferences of the attachment 32 and imaging element 34. Preferably, the link 36 is suitably flexible to make it easier for the imaging device to negotiate and accommodate the flexures along the body cavity.

Preferably, the wireless imaging element 34 has an imaging unit 42 and a light source 44 such as an LED, as shown in FIG. 5. In this embodiment, the imaging unit 42 and light source 44 are placed on the proximal end 46 of the wireless imaging element 34, although they may be placed at any suitable locations on the imaging element 34, including on the distal end or side of the imaging element 34 or both. Preferably, the imaging unit 42 faces backwards towards the main imaging device 26 and is oriented so that the imaging unit 42 and the main imaging device 26 can be used to provide different views of the same area. In the illustrated embodiment, the imaging unit 42 provides a retrograde view of the area, while the main imaging device 26 provides a front view of the area.

Since the main imaging device 26 and the imaging unit 42 of the detachable imaging device 30 face each other, the light source 24, 44 of one imaging device 26, 30 interferes with the other imaging device 30, 26. To reduce the interference, polarizer filters may be used with the imaging devices 26, 30 and light sources 24, 44. The main imaging device 26 and its light sources 24 may be covered by a first set of polarizer filters of the same orientation. And the wireless imaging unit 42 and light source 44 may be covered by a second set of polarizer filters orientated at 90° relative to the first set of polarizer filters. The use of polarizer filters to reduce light interference is well known and will not be described in detail herein.

As an alternative to polarizer filters, the imaging devices 26, 30 and their light sources 24, 44 may be turned on and off alternately to reduce or prevent light interference. In other words, when the main imaging device 26 and its light sources 24 are turned on, the imaging unit 42 and its light source 44 are turned off. And when the main imaging device 26 and its light sources 24 are turned off, the imaging unit 42 and its light source 44 are turned on. Preferably, the imaging devices 26, 30 and their light sources 24, 44 are turned on and off at a sufficiently high frequency that eyes do not sense that the light sources are being turned on and off.

The imaging element 34 may include a switch (not shown) that is used to connect power to the circuitries of the imaging element 34. When the switch is turned on, the circuitries of the imaging element 34 are activated and the imaging unit 42 starts capturing images and transmitting image signals. The switch can be a membrane switch mounted on the imaging element 34. The switch may be sealed with a biocompatible film (not shown), which can encase the imaging element or a section thereof to fully seal the switch.

In some embodiments, a wireless switch may be provided in placement of, or in addition to, the manual switch. The wireless transceiver of the imaging device 34 may continually search for a wireless enable signal from a particular address device or at a particular frequency. This signal enables a logic command to all the circuits in the imaging device 34 to switch from a low current sleep mode to a full current operating mode.

The wireless imaging element 34 preferably includes a housing 48a, 48b for accommodating the wireless imaging unit 42 and light source 44. The housing 48a, 48b of the wireless imaging element 34 preferably includes two housing elements 48a, 48b. The housing elements 48a, 48b preferably have features, such as pins and sockets, which allow the wireless imaging unit 42 and light source 44 to be securely mounted within the housing elements 48a, 48b. The housing elements 48a, 48b are sealingly attached to each other to maintain biocompatibility of the wireless imaging element 34 and prevent contaminants from entering the wireless imaging element 34. The housing elements 48a, 48b may be sealingly attached to each other in any suitable manner, including ultrasonic or friction welding or adhesive bonding. The housing 48a, 48b may include windows 50, 52 for the imaging unit 42 and light source 44, respectively. Preferably, each window 50, 52 is sealed with a thin clear cover that is attached to the housing 48a, 48b. In some embodiments, the windows 50, 52 may be the polarizer filters described previously.

In a preferred embodiment, a housing element 48a, the link 36, and the attachment 32 form a unitary unit made by means of, for example, injection molding. The other housing element 48b may be separately formed by means of, for example, injection molding. Preferably, the molded units are fabricated from a biocompatible material such as a biocompatible plastic. Alternatively, the housing elements 48a, 48b, the link 36, and the attachment 32 may be made as separate parts from the same material or different materials and then attached to one another to form the wireless imaging device 10.

Figure 8:
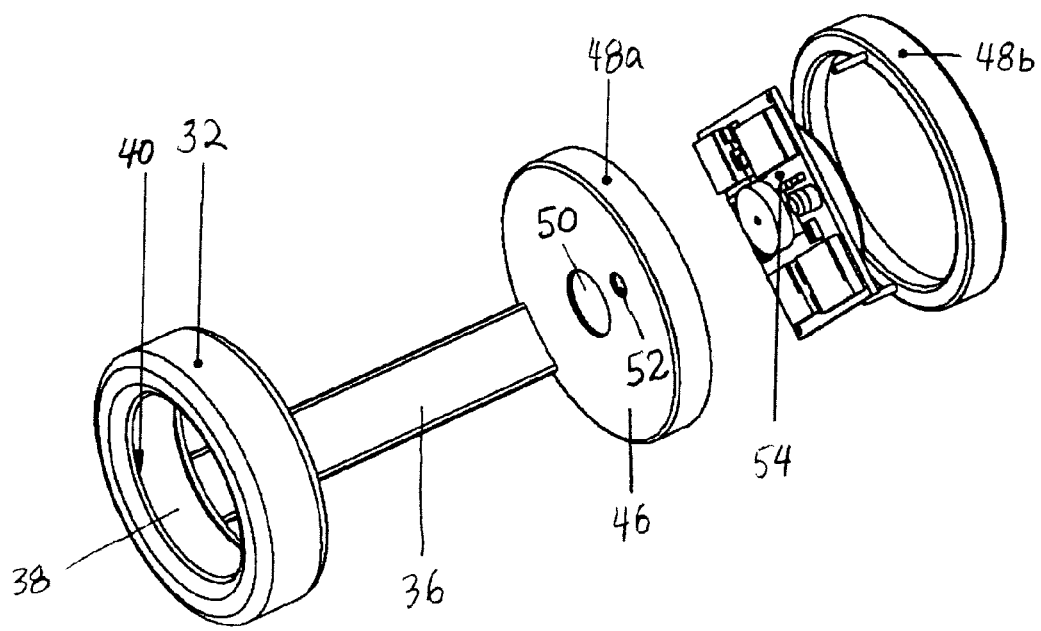
FIG. 8 is an exploded perspective view of the imaging element housing.
Figure 9:
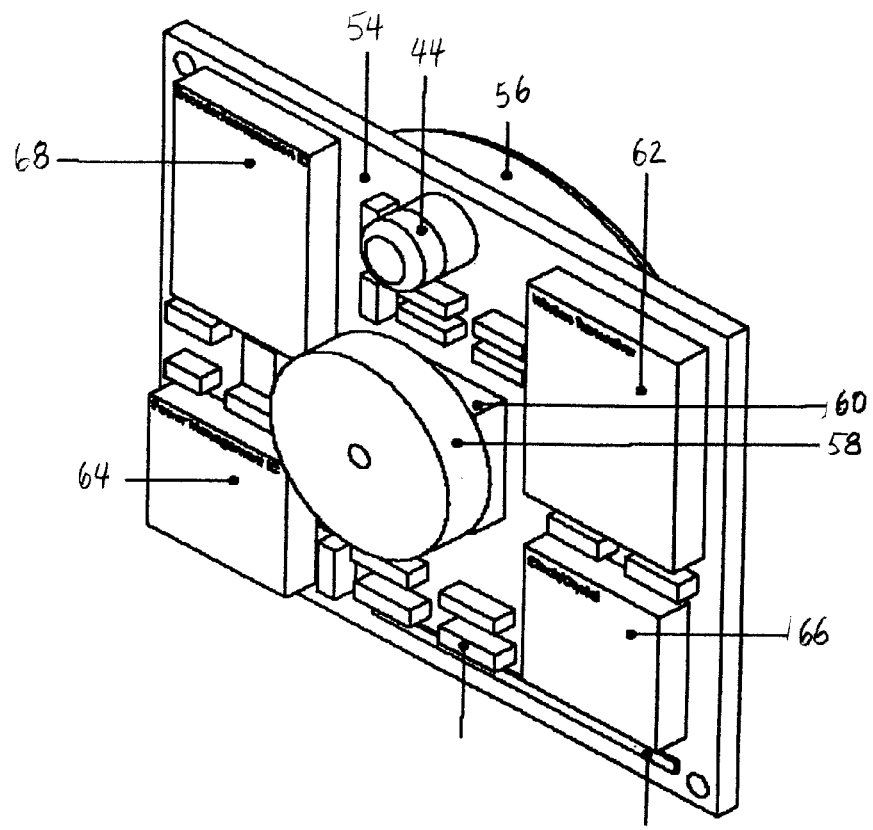
FIG. 9 is a perspective view of the imaging element printed circuit.

In the preferred embodiment shown in FIGS. 8 and 9, the circuitry for the wireless imaging unit 42 is formed on a printed circuit board (PCB) 54. The circuitry for the light source 44 may also be formed on the PCB 54. In this preferred embodiment, the circuitries for the imaging unit 42 and light source 44 are mounted on one side of the PCB 54, and a power source 56, such as a button battery cell, is clipped onto the other side of the PCB 54. The wireless imaging element 34 may include a lens 58, image sensor 60, wireless transceiver 62, power management unit 64, clock or crystal 66, and signal processing unit 68 as required by wireless communication. The positive and ground power clips (not shown) holding the power source 56 are connected to the power and ground planes of the PCB 54 respectively to supply power to the circuitries on the PCB 54.

The image sensor 60 may be any suitable device that converts light incident on photosensitive semiconductor elements into electrical signals. Such a device may detect color or black-and-white images. The signals from the sensor are digitized and used to reproduce the image. Two commonly used types of image sensors are Charge Coupled Devices (CCD) such as LC 99268 FB produced by Sanyo of Osaka, Japan and Complementary Metal Oxide Semiconductor (CMOS) camera chips such as the OVT 6910 produced by OmniVision of Sunnyvale, Calif.

The image data acquired by the image sensor 60 are transmitted to the signal processing unit 68 for processing. The processing may include one or more of multiplexing, encoding into radio frequencies, and compression. The wireless protocol used for image data transmission preferably is approved for medical use and meets the data rate requirements for the image sensor output. Suitable wireless protocols include, for example, the 802.11 and Bluetooth standards. The Bluetooth standard operates in the industrial, scientific and medical band (ISM band), has low transmit power, and causes minimal interference. The output formats for the image sensor 60 and the integrated circuits for image signal processing are well known in the electronics industry and are not explained in further detail. Once the image signal is converted to a suitable format, the wireless transceiver 62 transmits the data to an external control box over the operation frequency. Examples of wireless frequency bands used for similar devices include the 900 MHz and 2.4 GHz bands. Once received by a wireless receiver or transceiver of the external control box, the image signal is fed to a signal processing circuit which converts it to a video signal such as NTSC composite or RGB. This video signal is then sent to a suitable connector for output to a display device such as a monitor or television. In some embodiments, the images from the detachable imaging device 30 and from the main imaging device 26 can be shown together on the same display device.

The external control box may include a PCB mounted circuitry in a housing which transmits, receives and processes wireless signals. The external control box has one or more of a wireless transceiver, AC receptacle, decoding circuitry, control panel, image and signal processing circuitry, antenna, power supply, and video output connector.

The external control box may also be used as an interface to the patient records database. A large number of medical facilities now make use of electronic medical records. During the procedure relevant video and image data may need to be recorded in the patient electronic medical records (EMR) file. The signal processing circuit can convert image and video data to a format suitable for filing in the patient EMR file such as images in .jpeg, tif, or .bmp format among others. The processed signal can be transmitted to the medical professional's computer or the medical facilities server via a cable or dedicated wireless link. A switch on the control panel can be used to enable this transmission. Alternatively the data can be stored with a unique identification for the patient in electronic memory provided in the control box itself. The signal processing circuit can be utilized to convert the video and image data to be compatible with the electronic medical records system used by the medical professional. The processing may include compression of the data. A cable or a wireless link may be used to transmit the data to a computer.

The image and signal processing circuitry of the external control box includes one or multiple integrated circuits and memory as needed along with associated discrete components. This circuit allows the video signals to be processed for enhancing image quality, enabling still images to be extracted from the video and allow conversion of the video format to provide multiple output formats. These functions can be interfaced for access via the control panel.

The external control box may be used to adjust the parameters of the imaging sensor 60. Preferably, the image sensor 60 allows different parameters such as brightness, exposure time and mode settings to be adjusted. These parameters may be adjusted by writing digital commands to specific registers controlling the parameters. These registers can be addressed by their unique numbers and digital commands can be read from and written to these registers to change the parameters. The control box is used to control these parameters by transmitting data commands to these registers through the wireless protocol. The signal processing circuit on the detachable imaging device 30 receives and then decodes these signals into commands and feeds them to the image sensor. This allows the various parameters to be adjusted.

In some embodiments of the present invention, the power source 56 of the detachable imaging device 30 is a rechargeable power source. The rechargeable power source can be recharged in any suitable manner. For example, the rechargeable power source may be recharged via pins provided on the detachable imaging device. The pins preferably are made from a biocompatible material and retain its biocompatibility after sterilization up to a required number of times.

Alternatively, the rechargeable power source may be charged via inductive charging. One advantage of inductive charging is that it does not required physical contact between the charger and the detachable imaging device. This allows the detachable imaging device to be fully sealed without any circuit components or metals such as the charge pins being exposed to body liquids.

In operation, the power switch may be turned on first to activate the detachable imaging device 30. At this point, the detachable imaging device 30 begins transmitting captured digital images wirelessly to the external control box. The control box then processes the image signals and sends them to a display so that a medical professional can visualize the images in real time. Once the detachable imaging device 30 is turned on, it can be attached to the distal end region of the endoscope's insertion tube 12, as shown in FIGS. 1 and 2. At this point, the main imaging device 26 provides a front view of an area, while the detachable imaging device 30 provides a rear or retrograde view of the same area. During the medical procedure, the endoscope is inserted into a patient with the detachable imaging device 30 attached to the distal end region of the insertion tube 12. The medical professional can simultaneously visualize images from the main imaging device 26 and from the attached imaging device 30. Lesions hidden from the main imaging device 26 behind folds and flexures can now be viewed by the medical professional from the images provided by the detachable imaging device 30. When the procedure is complete, the endoscope is removed from the patient, and the detachable imaging device 30 can be detached from the distal end region of the endoscope's insertion tube 12.

The control panel of the external control box can be used to adjust the parameters of the detached imaging device 30 to achieve an optimum image quality. Still images can be obtained using the control panel. During the procedure, relevant video and image data may be recorded in the patient's electronic medical records (EMR) file.

Figure 10:
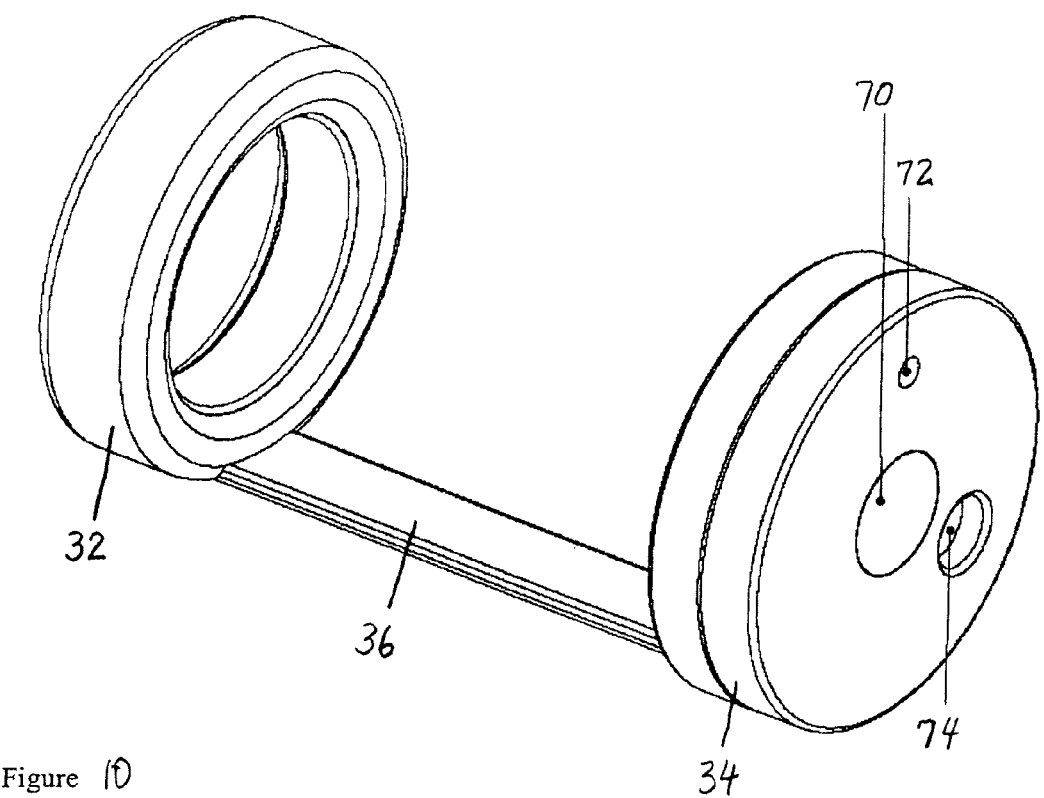
FIG. 10 is a perspective view of a detachable imaging device with a forward viewing imaging unit, a forward facing light source, and a channel.

The wireless imaging element 34 may additionally include a forward viewing imaging unit 70 and a forward facing light source 72, as shown in FIG. 10. This forward viewing imaging unit 70 allows more effective navigation of the endoscope 10. Additionally, to allow an accessory to reach the area in front of the wireless imaging element 34, the wireless imaging element 34 may be configured so as not to obstruct one or more channels 22 of the insertion tube 12. For example, the wireless imaging element 34 may be made small enough so that it does not obstruct one or more channels 22 of the insertion tube 12. Alternatively, the wireless imaging element 34 may include a channel 74 (FIG. 10) aligned with a channel 22 of the insertion tube 12. This channel 74 allows an accessory to reach the area in front of the wireless imaging element 34.

Figures 11A, 11B:
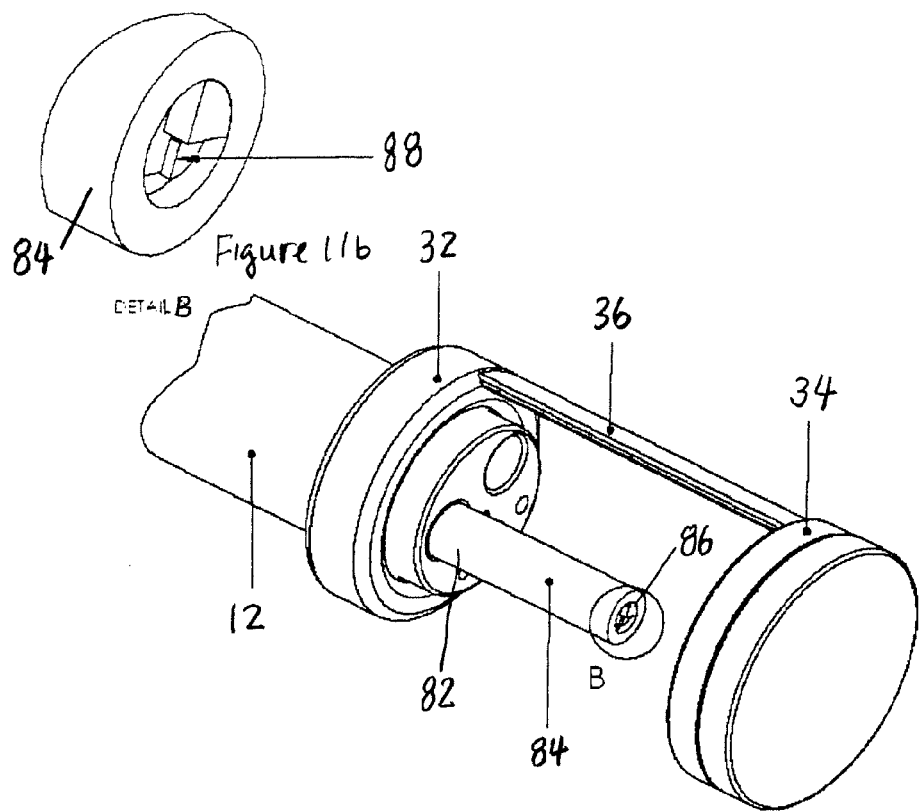
FIGS. 11a, 11b, 12a, and 12b show a support mechanism of an endoscope of the present invention.
Figures 12A, 12B:
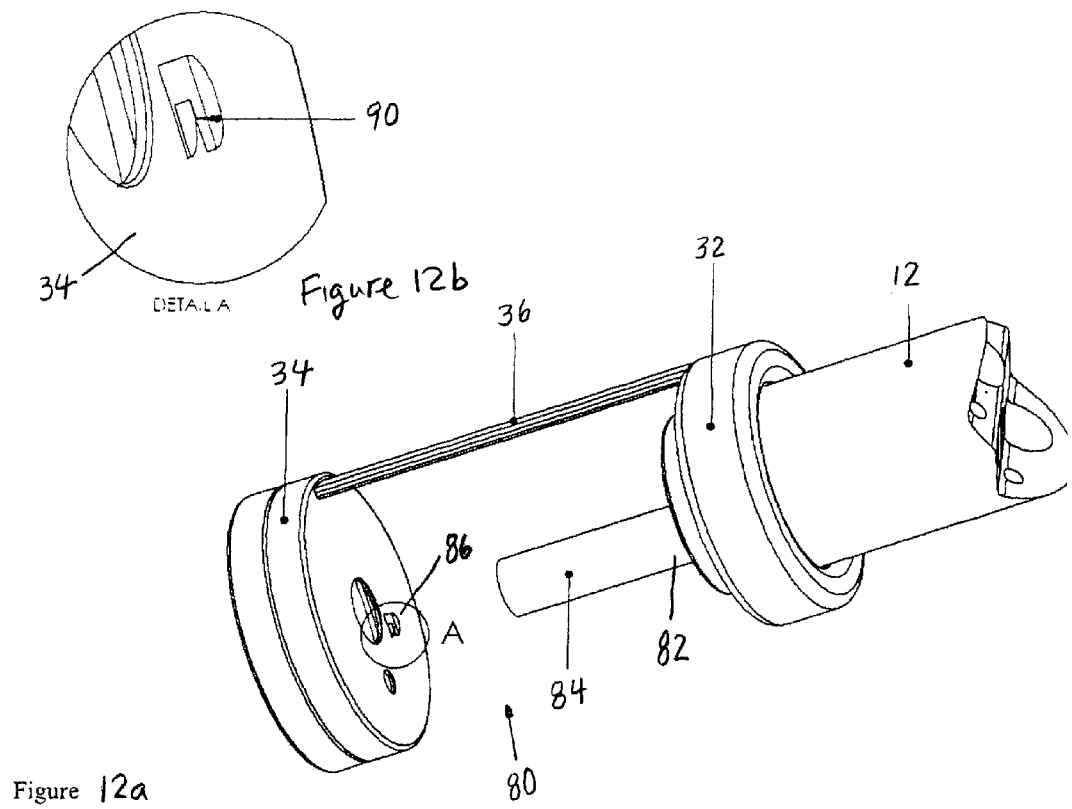

The endoscope 10 may further include a support mechanism, which increases the rigidity of the detachable imaging device 30 during insertion of the endoscope 10 into the body. This support mechanism preferably reduces or eliminates the bending of the link 36 of the detachable imaging device 30 during insertion. An embodiment 80 of the support mechanism is shown in FIGS. 11a, 11b, 12a, and 12b. The exemplary support mechanism 80 includes a rod 82 that is rigid at its distal end region 84 but is otherwise flexible. The exemplary support mechanism 80 may further include a locking mechanism 86 that locks the distal end of the rod 82 to the wireless imaging element 34. As shown in FIGS. 11b and 12b, the lock mechanism 86 includes mating grooves 88, 90 that are disposed on the distal end of the rod 82 and the wireless imaging element 34, respectively. The grooves 88, 90 can be interlocked by applying a torque to turn the rod 82 at the proximal end of the insertion tube 12, and can be unlocked by applying a torque in the opposite direction. The proximal end (not shown) of the rod 82 can be locked to the channel entry port to secure the locking mechanism 86 in the locked position.

Before the insertion of the endoscope 10 in the body, the rod 82 is introduced from the proximal end of the insertion tube 12 into a channel 22 of the insertion tube 12, and the locking mechanism 86 locks the distal end of the rod 82 to the wireless imaging element 34. At this position, the rigid distal end region 84 of the rod 82 keeps the detachable imaging device 30 rigid. After the insertion of the endoscope 10 in the body, the locking mechanism 86 can be unlocked, and the rod 82 can be retracted from the channel 22 of the insertion tube 12.

Figure 13:
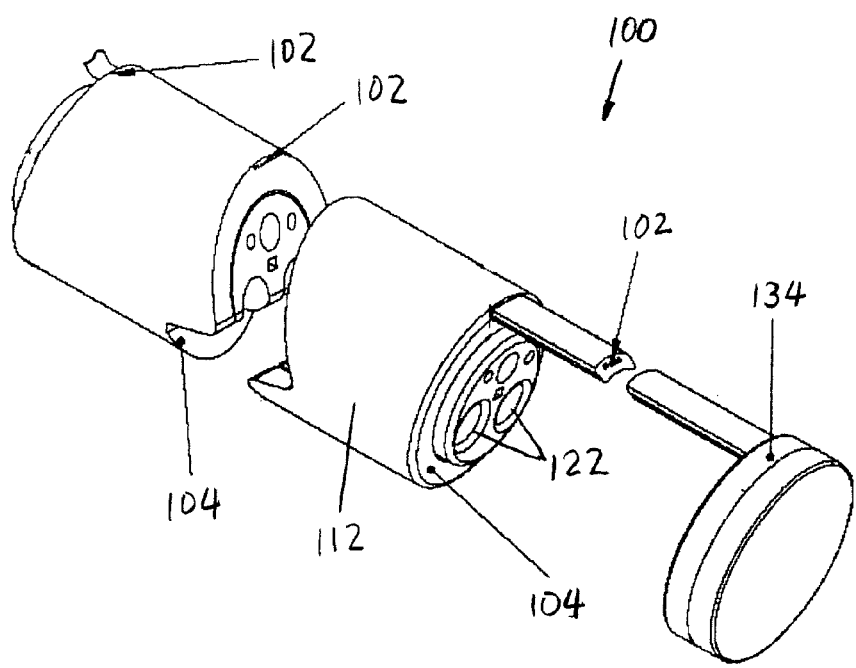
FIG. 13 shows an endoscope according to another embodiment of the present invention.

In some embodiments of the present invention, as shown in FIG. 13, an endoscope 100 may include a detachable imaging device 134 that uses wires 102 to communicate with the external control box, including transmitting video signals to the external control box and receiving power and control signals from the external control box. With this arrangement, the operation of the detachable imaging device 134 is not limited by battery life. As shown in FIG. 13, the wires 102 may be embedded in a sheath 104 which slides over the insertion tube 112 of the endoscope 100. This allows the channels 122 of the insertion tube 112 to be used by accessories and the endoscope 100 to retain all of its designed functions. Preferably, the sheath 104 is made from a biocompatible material such as latex, silicon and medical grade rubbers which are flexible enough to not restrict the movement of the insertion tube 112 and firmly grip the outer surface of the insertion tube 112. Alternatively this sheath 104 may replace the outer covering of the insertion tube 112 so that it would serve the dual function of covering the insertion tube 112 and the wires 102 without increasing the diameter of the insertion tube 112.

Figure 14:
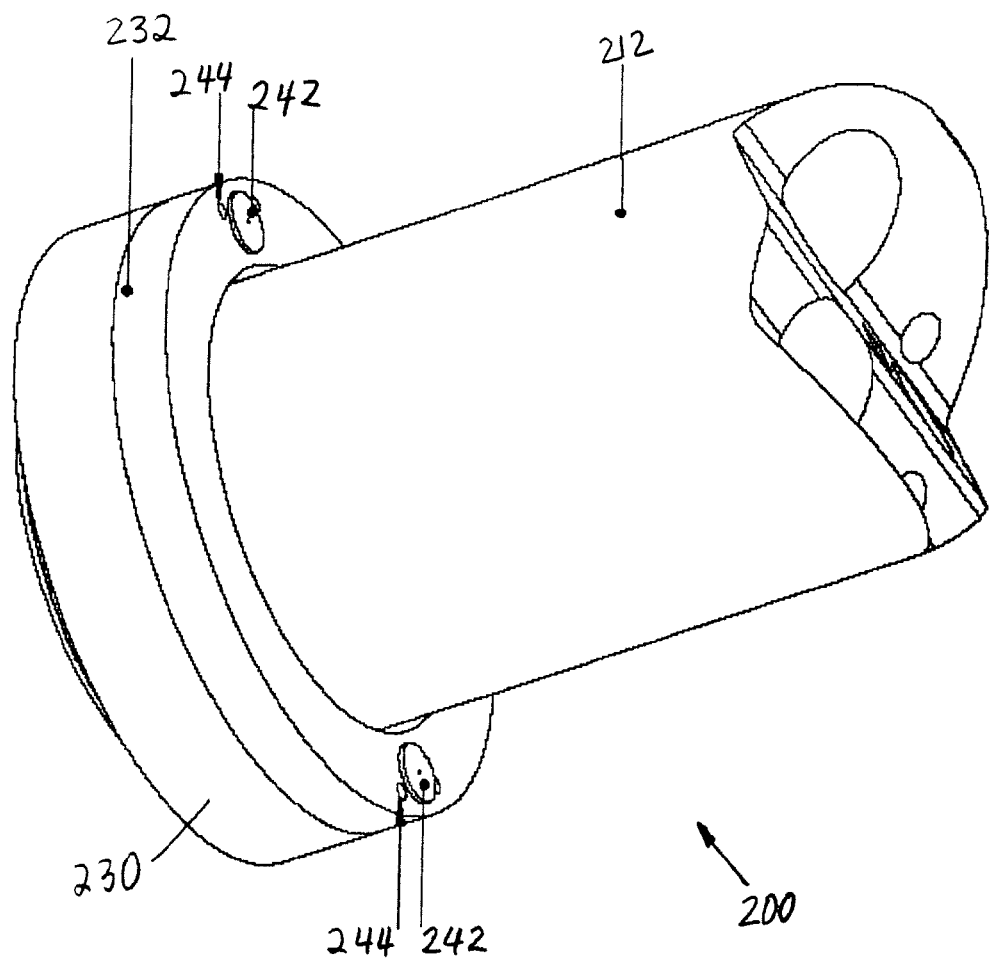
FIG. 14 shows an endoscope according to a further embodiment of the present invention.

FIG. 14 illustrates additional embodiment 200 of the present invention that includes an insertion tube 212 and an attachment 232 mounted on the distal end region of the insertion tube 212. This attachment 232 may have some or all of features of the attachment 32 shown in FIGS. 3 and 5. Additionally, the attachment 232 is configured to accommodate one or more imaging units 242 and light sources 244 of the endoscope 200. In other words, the entire detachable imaging device 230 is mounted on the distal end region of the insertion tube 212 and does not extend beyond the distal end of the insertion tube 212. The imaging units 242 and light sources 244 may be mounted at any suitable locations on the attachment 232 and may be oriented in any directions. In this embodiment, the imaging units 242 and light sources 244 are placed on a proximal end of the attachment 232 and face backwards, although they may be alternatively or additionally placed on a distal end and/or side of the attachment 232 and face forwards and/or sideways. The imaging units 242 and light sources 244 may be evenly spaced around the attachment 232. The images from the imaging units 242 may be incorporated or combined to form a larger or more complete view of the body cavity such as a 360° view of the body cavity. One advantage of the embodiment shown in FIG. 14 is the reduction or elimination of the mutual light interference between the main imaging device 26 and the imaging units 242 on the attachment 232 because the imaging units 242 and light sources 244 are placed behind the main imaging device and light sources on the distal end of the insertion tube 212.

Figure 15:
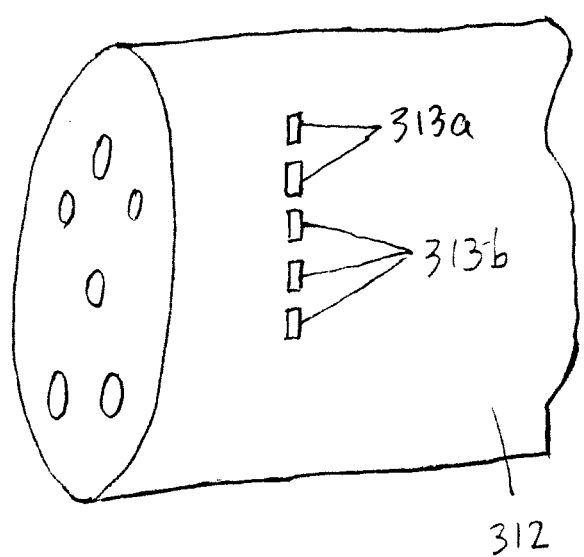
FIG. 15 shows an insertion tube having a connector for connecting a detachable imaging device to the wires in the insertion tube.

In a further embodiment of the present invention, an endoscope includes an insertion tube and a detachable imaging device detachably attached to the distal end region of the insertion tube. In this embodiment, the detachable imaging device communicates with the external control box via wires embedded in the insertion tube for power supply and/or data communication. The term "wires" is broadly defined to include any power and communication lines, such as metal wires and fiber optic cables. Preferably, as shown in FIG. 15, the insertion tube 312 has one or more connectors 313 for connecting the detachable imaging device to the wires in the insertion tube. In some embodiments, the one or more connector may be placed in the distal end region of the insertion tube. The one or more connectors may include one ore more power couplings 313a for providing power from the endoscope's base to the detachable imaging device and/or one or more video couplings 313b for coupling video images from the detachable imaging device to the base.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. An endoscope assembly comprising:
an insertion tube including a distal end region;
a main imaging device on the distal end region of the insertion tube; and
a detachable imaging device including:
an imaging element including a proximal surface and a distal surface;
a linking member including a distal portion and a proximal portion, the distal portion of the linking member being connected to the imaging element; and
an attachment member including an inner surface removably frictionally engageable with an outer surface of the distal end region of the insertion tube, the attachment member being connected to the proximal portion of the linking member, the attachment member being configured to detachably engage the imaging device to the insertion tube, wherein the imaging element is arranged to take images from a field of view that includes the main imaging device when the imaging element is used to view portions of a body cavity;
wherein the distal end region of the insertion tube includes a circular groove for receiving the attachment member.

2. The endoscope assembly of claim 1, wherein the attachment member includes an external surface portion that is made from a tacky or elastic material.

3. The endoscope assembly of claim 1, wherein the attachment member includes a clamp or a structure that provides a snap fit with the distal end region of the insertion tube.

4. The endoscope assembly of claim 1, wherein the linking member is an elongate, flat and straight bar.

5. The endoscope assembly of claim 1, wherein the linking member has a curved, circular or square cross-sectional profile.

6. The endoscope assembly of claim 1, wherein the linking member includes a transparent material.

7. The endoscope assembly of claim 1, further including a light source.

8. The endoscope assembly of claim 1, further including a polarized filter.

9. The endoscope assembly of claim 1, further including a membrane switch used to activate circuitry within the imaging device.

10. The endoscope assembly of claim 1, wherein the imaging element, linking member, and attachment member form a unitary unit made by injection molding.

11. The endoscope assembly of claim 1, wherein the imaging element includes a forward viewing imaging unit.

12. The endoscope assembly of claim 1, wherein the linking member is flexible.

13. The endoscope assembly of claim 1, further including a support mechanism configured to increase the rigidity of the imaging device.

14. The endoscope assembly of claim 1, wherein the imaging element is a wireless imaging element.

15. The endoscope assembly of claim 1, wherein the attachment member is configured to allow detachment of the imaging device to the distal end region of the insertion tube without damaging the insertion tube or the imaging device.

16. A method of using an endoscope assembly, comprising:
attaching a detachable imaging device to a distal end region of an insertion tube of an endoscope to form the endoscope assembly, wherein the distal end region of the insertion tube includes a first imaging element and wherein the detachable imaging device includes
a second imaging element;
a linking member including a distal portion and a proximal portion; and
an attachment member removably engageable with the distal end region of the insertion tube of the endoscope, the attachment member being connected to the proximal portion of the linking member, the attachment member being configured to detachably engage the imaging device to the endoscope, wherein the imaging element is arranged to take images from a field of view that includes the distal end region of the insertion tube when the imaging element is used to view portions of a body cavity; and
directing the distal end region of the insertion tube into a body cavity and viewing a portion of the body cavity with both the first imaging element and the detachable imaging device, the detachable imaging device providing a retrograde view of the portion of the body cavity and the first imaging element providing a front view of the portion of the body cavity;

wherein the endoscope assembly further includes a first light source and a second light source and the method further includes alternately turning on and off the first imaging element, and the second light source at a frequency sufficient such that a human eye cannot sense the alternation, wherein the first imaging element is on when the second light source is off and the first imaging element is off when the second light source is on.

17. The method of claim 16, wherein the linking member is an elongate, flat and straight bar.

18. The method of claim 16, wherein the endoscope assembly further includes a polarized filter.

19. The method of claim 18, wherein the imaging element is a wireless imaging element.

20. The method of claim 16, wherein the attachment member is configured to allow detachment of the imaging device from the distal end region of the insertion tube without damaging the insertion tube or the imaging device.

21. The method of claim 16, wherein the attachment member includes an external surface portion that is made from a tacky or elastic material.

22. The method of claim 16, wherein the attachment member includes a clamp or a structure that provides a snap fit with the distal end region of the insertion tube.

23. The method of claim 16, wherein the imaging element is a wireless imaging element.

24. The method of claim 16, wherein the attachment member is configured to allow attachment of the imaging device to the distal end region of the insertion tube without damaging the insertion tube or the imaging device.

25. The method of claim 16, wherein the distal end region of the insertion tube includes a circular groove for receiving the attachment member.

26. An endoscope assembly, comprising:
   an insertion tube including a distal end region;
   a first imaging device on the distal end region of the insertion tube; and
   a detachable imaging device including:
      an imaging element including a proximal surface and a distal surface;
      a linking member including a distal portion and a proximal portion; and
      an attachment member including an inner surface removably frictionally engageable with an outer surface of the distal end region of the insertion tube, the attachment member being connected to the proximal portion of the linking member, the attachment member being configured to detachably engage the detachable imaging device to the insertion tube, wherein the imaging element is arranged to take images from a field of view that includes the first imaging device when the imaging element is used to view portions of a body cavity;
   a first light source on the distal end region of the insertion tube; and
   a first polarizer filter covering the first light source, wherein the detachable imaging device includes:
      a second light source; and
      a second polarizer filter covering the imaging element, wherein the first imaging device and the imaging element are configured to view a portion of the body cavity, the imaging element configured to provide a retrograde view of the portion of the body cavity and the first imaging device configured to provide a front view of the portion of the body cavity, wherein the first and second polarized filters are configured to reduce light interference between the imaging element and the first light source.

27. The endoscope assembly of claim 26, wherein the first polarizing filter is part of a first set of polarizing filters covering the first imaging device and the first light source, and wherein the second polarizing filter is part of a second set of polarizing filters covering the imaging element and the second light source.

28. The endoscope assembly of claim 27, wherein the second set of polarizing filters is oriented at ninety degrees relative to the first set of polarizing filters.

29. A method of using an endoscope assembly, comprising:
   attaching a detachable imaging device to a distal end region of an insertion tube of an endoscope to form the endoscope assembly, the imaging device including:
      an imaging element;
      a linking member including a distal portion and a proximal portion; and
      an attachment member removably engageable with the distal end region of the insertion tube of the endoscope, the attachment member being connected to the proximal portion of the linking member, the attachment member being configured to detachably engage the imaging device to the endoscope, wherein the imaging element is arranged to take images from a field of view that includes the distal end region of the insertion tube when the imaging element is used to view portions of a body cavity;
   wherein the distal end region of the insertion tube includes a circular groove for receiving the attachment member.

30. The method of claim 29, wherein the distal end region of the insertion tube further includes a main imaging device.

31. The method of claim 30, further including directing the distal end region of the insertion tube into a body cavity and viewing a portion of the body cavity with both the main imaging device and the imaging device, the imaging device providing a retrograde view of the portion of the body cavity and the main imaging device providing a front view of the portion of the body cavity.

32. The method of claim 31, wherein the endoscope assembly further includes a polarized filter.

33. The method of claim 32, wherein the imaging element is a wireless imaging element.

34. The method of claim 31, wherein the endoscope assembly further includes a first light source and a second light source and the method further includes alternately turning on and off the main imaging device, the first light source, the imaging element and the second light source at a frequency sufficient such that a human eye cannot sense the alternation, wherein the main imaging device and first light source are on when the imaging element and second light source are off and the main imaging device and first light source is off when the imaging element and second light source are on.

35. The method of claim 29, wherein the linking member is an elongate, flat and straight bar.

36. The method of claim 29, wherein the attachment member is configured to allow detachment of the imaging device from the distal end region of the insertion tube without damaging the insertion tube or the imaging device.

37. The method of claim 29, wherein the attachment member includes an external surface portion that is made from a tacky or elastic material.

38. The method of claim 29, wherein the attachment member includes a clamp or a structure that provides a snap fit with the distal end region of the insertion tube.

39. The method of claim 29, wherein the linking member includes two or more poles.

40. The method of claim 29, wherein the imaging element is a wireless imaging element.

41. The method of claim 29, wherein the attachment member is configured to allow detachment of the imaging device to the distal end region of the insertion tube without damaging the insertion tube or the imaging device.

* * * * *